United States Patent [19]

Koehler et al.

[11] 4,273,760

[45] Jun. 16, 1981

[54] SHAMPOO COMPOSITIONS

[75] Inventors: F. Theodore Koehler, Plainfield; Albert L. Micchelli, Middletown; Frank A. Nowak, Jr., Somerville, all of N.J.

[73] Assignee: National Starch and Chemical Corporation, Bridgewater, N.J.

[21] Appl. No.: 75,720

[22] Filed: Sep. 14, 1979

Related U.S. Application Data

[63] Continuation of Ser. No. 9,572, Feb. 5, 1979, abandoned, which is a continuation of Ser. No. 833,281, Sep. 14, 1977, abandoned.

[51] Int. Cl.$^3$ .............................................. A61K 7/06
[52] U.S. Cl. ...................... 424/70; 252/542; 252/545; 252/547; 252/DIG. 2; 252/DIG. 3; 252/DIG. 13; 424/DIG. 2; 424/71; 424/81
[58] Field of Search ............................................ 424/70

[56] References Cited

U.S. PATENT DOCUMENTS

| | | | |
|---|---|---|---|
| 3,496,110 | 2/1970 | Shumway et al. | 424/70 X |
| 3,914,403 | 10/1975 | Valan | 424/70 |
| 4,180,084 | 12/1979 | Wegmuller et al. | 424/47 |

FOREIGN PATENT DOCUMENTS

| | | | |
|---|---|---|---|
| 2452032 | 5/1976 | Fed. Rep. of Germany | 424/70 |
| 2710468 | 10/1977 | Fed. Rep. of Germany | 424/70 |
| 748582 | 10/1970 | France | 424/70 |
| 1443426 | 7/1976 | United Kingdom | 424/70 |

OTHER PUBLICATIONS

Gulbekian, J. Soc. Co. Chem., 1970, vol. 21, pp. 471–482.

Primary Examiner—Dale R. Ore
Attorney, Agent, or Firm—Edwin M. Szala; Ellen T. Dec; Janet E. Hasak

[57] ABSTRACT

Hair conditioning shampoo compositions are described containing cationic polymers, anionic surfactants and optional nonionic surfactants. The shampoo compositions deposit the cationic polymer on the hair while the hair is washed using the shampoo, rendering the hair to be more manageable.

7 Claims, No Drawings

SHAMPOO COMPOSITIONS

This is a continuation of U.S. Application Ser. No. 009,572 filed Feb. 5, 1979, now abandoned which is a continuation of U.S. Application Ser. No. 833,281, filed Sept. 14, 1977, now abandoned.

BACKGROUND OF THE INVENTION

The present invention is directed to conditioning shampoo formulations prepared from specific cationic polymers, anionic surfactants and optional nonionic surfactants. The resultant shampoo formulations are economical to prepare, exhibit improved lathering and possess commercially acceptable conditioning properties.

The need for a shampoo formulation which conditions (i.e. renders the hair more manageable) as it cleans has long been recognized in the art. Thus, while conditioning agents for application to already shampooed hair have long been known, it has only been within recent years that conditioning shampoos have become available. A number of these shampoos are specially formulated for mildness and hence, low detergency, so as to leave a portion of the hair's natural oils behind. Consequently the hair soon looks and feels greasy and dirty. Other formulations contain certain oily components, such as polyglycols, fatty acid esters of glycols, natural or synthetic waxes or lanolin derivatives, which components are deposited on the hair during shampooing. The oily nature of such components, however, inhibits lathering of the shampoo and also contributes to the feeling of greasy, dirty hair soon after shampooing.

A third type of conditioning shampoo contains a cationic polymer which can deposit on the hair during shampooing to impart the desired degree of manageability while overcoming the previously described problem of greasiness development. The primary difficulty encountered in preparing such shampoo conditioners has been that of achieving a stable system without destroying the delicate balance of conditioning and other functional properties. Previous attempts to provide solubility of the conditioning polymer while achieving suitable cleaning and lathering as well as deposition of the polymer on the hair have resulted in the finding that specific polymers when incorporated with amphoteric surfactants (detergents), optionally in the presence of nonionic or ionic surfactants, will result in shampoo formulations which condition as they clean. Such findings are due to the superior compatibility of the amphoterics with the commonly used cationic polymers thereby allowing maximum deposition of the polymer onto the hair during shampooing.

Thus, U.S. Pat. No. 4,009,256 issued Feb. 22, 1977 and assigned to the assignee herein, discloses a conditioning shampoo comprising an aqueous solution of (1) a cationic polymer which is a water-soluble acid salt of an aminoalkyl ester of a carboxylic acid polymer, (2) an amphoteric detergent, and (3) optionally, at least one nonionic surfactant or at least one ionic surfactant or a combination thereof, wherein any plurality of ionic surfactants utilized consists of those of the same ionogenic class. The necessity for employing the amphoteric detergent in such formulations is supported and reinforced by substantially all the patents directed to conditioning shampoos. Thus, U.S. Pat. Nos. 3,313,734; 3,962,418; 2,999,069; 3,055,836; 3,996,146 and 3,400,198, among others, require the presence of an amphoteric or polar non-ionic component in order that the conditioning polymer be compatible with the remaining ingredients in the shampoo formulation. Of all the pertinent art known to applicants, only U.S. Pat. No. 3,816,616 discloses a conditioning shampoo which does not require the presence of a compatibilizing agent and such teaching is directed only to the use of one very specific cationic polymer—a quaternized modified cellulosic polymer.

The primary disadvantages to the requirement for an amphoteric detergent or surfactant to be present in conditioning shampoo formulations are related to their high cost and weak foaming ability relative to the anionic surfactants available. Thus the use of amphoteric surfactants substantially increases the cost of producing conditioning shampoos, thereby limiting the consumer market to which the products may be directed.

It is therefore an object of the present invention to provide a conditioning shampoo which can be prepared in the absence of an amphoteric component.

It is a further object to prepare an economical, effective conditioning shampoo.

These and other objects will be apparent from the description which follows.

SUMMARY OF THE INVENTION

We have now found that a novel, highly acceptable conditioning shampoo composition meeting the aforementioned objectives comprises an aqueous solution consisting essentially of:

(1) from 0.1 to 10.0%, by weight of the total solution, of a cationic polymer having a molecular weight of 5,000 to 250,000 and selected from the group consisting of the water-soluble acid salts of aminoalkyl esters of (a) homopolymers of homopolymerizable unsaturated carboxylic acids having 3 to 5 carbon atoms; (b) copolymers of copolymerizable mixtures of said acids; and (c) copolymers of unsaturated carboxylic acids having 3 to 5 carbon atoms and at least one copolymerizable ethylenically unsaturated comonomer selected from the group consisting of vinyl acetate, vinyl propionate, vinyl methyl ether, vinyl ethyl ether, the $C_1$–$C_8$ alkyl esters of maleic and fumaric acids, amides of acrylic and methacrylic acids, and the $C_1$–$C_{18}$ alkyl and $C_2$–$C_4$ hydroxyalkyl esters of acrylic and methacrylic acids wherein the copolymers of group (c) are prepared with at least 50 mole percent of the unsaturated carboxylic acid component;

(2) from 5.0 to 30.0%, by weight active solids based on the weight of the total solution, of at least one anionic surfactant; and (3) from 0 to 10.0%, by weight active solids based on the weight of the total solution, of at least one nonionic surfactant.

When used in the usual and conventional manner in shampooing hair, the resultant shampoos of the described formulation exhibit both cleaning and conditioning properties. Moreover, due to the relatively high level of anionic surfactant present in the formulations, these novel shampoos are characterized by superior lathering, an attribute widely desired in the consumer marketplace.

DETAILED DESCRIPTION OF THE PREFERRED EMBODIMENTS

The cationic polymers useful in the conditioning shampoos of the present invention are those employed in U.S. Pat. No. 4,009,256 discussed hereinabove, the disclosure of which is incorporated herein by reference. Among these various cationic polymers are included the mineral acid salts of the amino-alkyl esters of homo- and copolymers of unsaturated carboxylic acids having from 3 to 5 carbon atoms, for example, acrylic acid, methacrylic acid, crotonic acid, ethacrylic acid, fumaric acid, maleic acid and itaconic acid, and the aminoalkyl groups containing from 2 to 6 carbon atoms. Useful aminoalkyl groups include, for example, aminoethyl, N-methyl aminoethyl, N-ethyl aminoethyl, 2-aminopropyl and t-butyl aminoethyl, with the aminoethyl being preferred.

More specifically, the useful polymers include the salts of the aminoalkyl esters of (a) homopolymers of homopolymerizable unsaturated carboxylic acids having 3 to 5 carbon atoms; (b) copolymers of copolymerizable mixtures of acids, and (c) copolymers formed of unsaturated carboxylic acids having 3 to 5 carbon atoms and at least one copolymerizable ethylenically unsaturated comonomer selected from the group consisting of vinyl acetate and vinyl propionate; vinyl methyl ether and vinyl ethyl ether; the $C_1$–$C_8$ alkyl esters of maleic and fumaric acids, for example, diethyl fumarate, dioctyl fumarate, dibutyl maleate, dioctyl maleate, monobutyl maleate, monomethyl fumarate, and monooctyl fumarate; amides of acrylic and methacrylic acids, for example, acrylamide, N-methyl acrylamide and methacrylamide; and the $C_1$–$C_{18}$ alkyl and $C_2$–$C_4$ hydroxyalkyl esters of acrylic and methacrylic acids. Specific examples of the latter class of comonomers includes methyl acrylate, ethyl acrylate, butyl acrylate, octyl acrylate, dodecyl acrylate, stearyl acrylate, hydroxyethyl acrylate, hydroxypropyl acrylate, as well as the corresponding methacrylate esters. Preferred comonomers include the amides and the $C_1$–$C_{18}$ alkyl and $C_2$–$C_4$ hydroxyalkyl esters of acrylic and methacrylic acids.

It will be recognized that, for the purposes of the present invention, the copolymeric mixture of copolymerizable carboxylic acids of group (b) may contain the various monomeric components in any proportion. However, in the case of the copolymers of group (c), there must be present at least 50 mole percent, and preferably 75 mole percent, of the unsaturated carboxylic acid component.

Particularly preferred cationic polymers for use herein are the phosphate salts of poly(aminoethyl acrylate) or poly(aminoethyl acrylate hydroxypropyl acrylate) or a terpolymer of an aminoalkyl ester of an ethylenically unsaturated carboxylic acid, an amide of an ethylenically unsaturated carboxylic acid, and a hydroxyalkyl ester of an ethylenically unsaturated carboxylic acid wherein said cationic polymer has a molecular weight between about 25,000 and 100,000.

With regard to the preparation of cationic polymers useful in the practice of this invention, the practitioner will recognize that such materials may be commercially available or may normally be synthesized either (1) by polymerizing monomers which have the functional aminoalkyl ester groups attached or (2) by subsequently affixing said groups to a base polymer such as the homopolymer of an ethylenically unsaturated carboxylic acid or a copolymer formed with at least one ethylenically unsaturated carboxylic acid and one or more copolymerizable comonomers. For example, the first method would typically involve the homopolymerization of one of the following: t-butylaminoethyl methacrylate dimethylaminoethyl methacrylate, or the copolymerization of any one of the foregoing compounds with one or more of the above-mentioned copolymerizable comonomers. Such methods are disclosed in, inter alia, Piloni, U.S. Pat. No. 2,979,491; P. L. deBenneville, U.S. Pat. No. 2,744,884; and in Mowry et al., U.S. Pat. No. 2,625,471. The second method wherein the functional aminoalkyl ester groups are affixed to the base polymer may be carried out according to the process taught in, inter alia, assignee's Fertig et al. U.S. Pat. No. 3,372,149, the disclosure of which is incorporated herein by reference. Regardless of the means of synthesis selected, a well known free radical polymerization procedure is usually entailed. These compounds, upon utilization in accordance with this invention, are all characterized by their ability to display the desirable hair conditioning properties.

The anionic surfactants employed in the present shampoo compositions are also discussed in U.S. Pat. No. 4,009,256 and include the higher fatty alcohol sulfates such as, for example, sodium lauryl sulfate; the alkylaryl sulfonates, e.g. sodium or potassium isopropylbenzene sulfonates, isopropyl naphthalene sulfonates; the alkali metal higher alkyl sulfosuccinates, e.g. sodium octenyl sulfosuccinate, sodium N-methyl-N-palmitoyl taurate, sodium oleyl isethionate; the alkali metal salts of alkylarylpolyethoxyethanol sulfates or sulfonates, e.g., the sodium t-octyl-phenoxypolyethoxyethyl sulfates and sulfonates having from 1 to 5 oxyethylene units.

Aside from the various types of anionic, synthetic detergents mentioned above, the laurylsulfoacetamide type, sulfated fatty acyl monoethanolamide, sodium stearate, and the sodium salts of the long chain ($C_8$–$C_{18}$) acyl-sarcosinates made by condensing a fatty acid chloride with N-methyl glycine, are also useful in the practice of this invention.

If desired, various nonionic surfactants may also be employed including the polyoxyalkylene alkyl ethers and condensates of alkylene oxides with fatty acids.

With regard to proportions, these novel conditioning shampoos generally contain from 0.1–10.0%, preferably 0.5 to 2.0% by weight of the total solution of the cationic polymer, 5.0 to 30.0%, preferably 10.0 to 20.0%, by weight of the total solution of the anionic surfactant and 0 to 10.0%, preferably 2.0 to 8.0%, by weight of the total solution of the nonionic surfactant.

The practitioner will recognize that the actual concentration of any particular cationic polymer used in a given conditioning shampoo preparation encompassed within this invention may vary within the prescribed range, for many reasons. For example, the maximum usable concentration will depend on the nature and molecular weight of the polymer, its compatibility with the particular surfactant employed and any optional ingredients used, the degree of pH adjustment, if required, and the neutralizing agent utilized.

Since some of the ingredients employed in the practice of this invention tend to support bacterial growth, a small amount of a preservative should be added to prevent such microbial growth. Though other well known preservatives and bactericides such as formaldehyde may be employed, we prefer to use the lower molecular weight alkyl p-hydroxybenzoates.

Optional ingredients, in addition to the nonionic surfactant described hereinabove, may be incorporated into the conditioning shampoo compositions of this invention in order to modify certain properties thereof.

Among these additives may be included: emollients and lubricants such as glycols, esters, and glycerine; lanolin compounds; protein hydrolyzates and other protein derivatives; ethylene oxide adducts, and cholesterol derivatives; dyes and other colorants, perfumes, and ultraviolet light absorbers, chelating agents and foam boosters. The polymeric conditioning agents show little or no tendency to react with such additives.

The novel, hair conditioning shampoo compositions of this invention are prepared by dispersing the resin depositing, cationic polymer and the anionic surfactant in water with moderate agitation. When a homogeneous system is obtained, any optional ingredients may be added under appropriate conditions. For instance, the addition of a compound such as an amide may require heating the solution to ensure dispersion of the melted waxy material and the subsequent addition of a particular compound such as a perfume will require adequate cooling, prior thereto, to avoid its volatilization. Also it may be desired to slightly adjust the pH level.

The pH adjusting agent and quantity to be used should be chosen to ensure maximum efficiency of a shampoo composition which will not damage the hair or irritate the eyes or skin. A preferred pH range, for the solutions prepared according to this invention, is from 3.5–7.0. Since the initial pH level of the shampoo compositions herein is usually between 5.0 and 6.0, it is preferred that weak acids such as citric acid, acetic acid, phosphoric acid, and the like and weak bases such as the alkanolamines, e.g. triethanolamine, diethanolamine, etc. be used as pH adjusting agents.

The resulting shampoo formulations exhibit all of the characteristics required of such products. They are capable of thoroughly cleaning the hair with superior foaming and rinsability of lather while depositing thereon a film which conditions the hair. These conditioning properties are noticeable after only one shampooing but increase substantially over time upon repeated use of the shampoo formulations of this invention.

The films deposited on the hair fibers by the present, novel shampoo compositions possess good antistatic properties, adhere well to the hair, allow the hair to be readily recombed, do not become tacky when exposed to high humidities and are easily removed by conventional shampoos. In addition, it should be noted that the conditioning shampoos of this invention remain effective in cleaning the hair and imparting the desired manageability, wet and dry combing and, at times, curl retention properties thereto, when optional, conventional ingredients are incorporated therein.

The combined hair cleaning and conditioning procedure used in practicing this invention is essentially the same as that of a conventional shampoo technique. Ordinarily the hair is wetted; the shampoo preparation, as a concentrate, is applied and thoroughly massaged throughout the hair to ensure even distribution of the lather thus produced; the hair is then rinsed free of the lather, wiped partially dry, combed, and fixed in the desired configuration in which it is allowed to dry. The dried hair is then combed out into the desired set. Obviously, the practitioner may elect to repeat the cycle or otherwise vary from this technique without departing from the scope of this invention.

The invention will now be further illustrated by, but not intended to be limited by, the following examples. The quantities of all ingredients are given in parts by weight, of the total formulation, unless specified otherwise.

EXAMPLES I–VI

These examples illustrate the preparation and effectiveness of a shampoo composition comprising various levels of a salt of an aminoalkyl ester of a ethylenically unsaturated carboxylic acid in combination with a variety of anionic surfactants.

Shampoo compositions were prepared using the ingredients and amounts shown in Table I. In each instance, the polyethylene glycol (PEG 400) monostearate was dissolved in water and the anionic surfactant added. When the mixture became homogeneous, the cationic polymer was slowly added with agitation, followed by addition of the lauric diethanolamide (a nonionic foam booster). After continued mixing, a uniform, clear shampoo solution resulted.

Each of the shampoo compositions was then evaluated as follows:

Approximately ⅛ gram of shampoo was uniformly applied to wet swatches of virgin, brown European hair, each 10 inches in length and weighing approximately 2 grams. Each swatch was gently massaged for about 2 minutes to produce lather and the hair was then rinsed with warm tap water for one minute. The foregoing steps were repeated. Excess water was then squeezed out of the thoroughly rinsed swatches by running them between two fingers. Swatches were then found to be easily combed through while wet. Swatches were soft and silky and easy to comb when dry.

EXAMPLE VII

Shampoo compositions according to the present invention were prepared using a plurality of anionic surfactants and adopted for use on normal, oily and dry hair as shown in Table II.

In each case, the Condanol SBFA/3 was dissolved in water and the cationic polymer added with agitation. After the solution became homogeneous, the remaining ingredients were added with agitation continuing until a uniform mixture was formed.

TABLE I

| Ingredients | I | II | III | IV | V | VI |
|---|---|---|---|---|---|---|
| Phosphate salt of poly(aminoethyl acrylate hydroxypropyl acrylate) (18% aqueous solution)-Catrex supplied by National Starch and Chemical Corp. | 5.60 | 11.20 | 5.60 | 11.20 | 5.60 | 11.20 |
| Sodium lauryl ether sulfate (2 moles ethylene oxide) (25% aqueous solution) - Maprofix ES supplied by Onyx Chemical Co. | 20.00 | 35.00 | x | x | x | x |
| Triethanolamine lauryl sulfate (40% aqueous solution)-Maprofix TLS-500C supplied by Onyx Chemical Co. | x | x | 15.00 | 20.00 | x | x |

TABLE I-continued

| Ingredients | I | II | III | IV | V | VI |
|---|---|---|---|---|---|---|
| Disodium salt of a sulfo-succinate half ester of an alkanolamide (30% aqueous solution) - Monamate OPA-30 supplied by Mona Industries. | x | x | x | x | 45.00 | 45.00 |
| Modified lauric diethanolamide-Monamid 716 supplied by Mona Industries. | 2.00 | 2.00 | 2.00 | 2.00 | 2.00 | 2.00 |
| PEG (400) Monostearate (non-ionic foam booster, stabilizer, thickener) | 3.00 | 3.00 | 3.00 | 3.00 | 3.00 | 3.00 |
| Distilled water | 69.40 | 48.80 | 74.40 | 63.80 | 44.40 | 38.80 |

TABLE II

| | Parts by Weight | | |
|---|---|---|---|
| Ingredients | Normal Hair | Oily Hair | Dry Hair |
| Distilled water | 24.90 | 16.90 | 31.90 |
| Fatty alcohol ether sulfosuccinate (40% aqueous solution)Condanol SBFA/3 supplied by Dutton & Reinisch Ltd. | 40.00 | 40.00 | 40.00 |
| Phosphate salt of poly(aminoethyl acrylate hydroxypropyl acrylate) (18% aqueous solution) Catrex supplied by National Starch and Chemical Corp. | 5.60 | 5.60 | 5.60 |
| Lanolin Derivative Emolient - Lanexol AWS supplied by Croda. | x | x | 1.00 |
| Sodium lauryl ether sulfate (2 moles ethylene oxide) (25% aqueous solution) - Maprofix ES supplied by Onyx Chemical Co. | 10.00 | 15.00 | 5.00 |
| Triethanolamine lauryl sulfate (40% aqueous solution) - Maprofix TLS-500C supplied by Onyx Chemical Co. | 15.00 | 20.00 | 10.00 |
| Polyoxyethylene (4) lauryl ether - Brij 30 supplied by ICI. | 2.00 | 1.00 | 3.00 |
| Modified lauric diethanolamide - Monamid 716 supplied by Mona Industries | 2.00 | 1.00 | 3.00 |
| Sodium Chloride | 0.50 | 0.50 | 0.50 |
| Dye, Perfume, Preservative | q.s. | q.s. | q.s. |
| 10% Phosphoric acid | to pH 6-7 | to pH 6-7 | to pH 6-7 |

After filtering, the shampoo formulations were evaluated as described in Examples I–VI and all three found to give superior results leaving the hair clean, and manageable with good body.

EXAMPLE VIII

Shampoo compositions similar to those described in Example VII were prepared using the procedure disclosed therein and then evaluated in the manner described hereinbelow. The shampoo compositions are as follows:

TABLE III

| Ingredients | Amounts |
|---|---|
| Distilled water | q.s. to 100% |
| Monamate OPA-30 | 25.95 |
| Catrex | 0 to 7% |
| Maprofix ES | 10.85 |
| Maprofix TLS-500C | 14.16 |
| Brij 30 | 1.89 |
| Monamid 716 | 2.36 |
| NaCl | 0.30 |
| Fragrance | 0.09 |
| Tetrasodium EDTA (a chelating agent) Versene 100 supplied by Dow | 0.24 |
| Methyl-p-hydroxy benzoate (preservative) | 0.09 |
| Propyl-p-hydroxy benzoate (preservative) | 0.01 |

Theory of Test Method: Hair is known to contain a number of "free" anionic (acidic) sites and "free" cationic (basic) sites which can bind chemical species of the opposite ionogenic class. It has been shown that the basic groups will readily and reproducibly combine with Orange II dye in a formic acid medium. The degree of combination is easily determined through measurement of Orange II depletion from a standard solution in contact with hair under controlled conditions.

It is further known that the deposition of a cationic polymer onto the hair increases the number of basic sites per unit of hair. This modification, therefore, adds to the dye combining capacity of the hair. The degree of cationic polymer pickup by the hair is determined by relating dye combining capacity of the hair treated with the test material to hair treated with a control sample.

Preparation of Orange II Stock Solution: The acid form of Orange II was prepared by acidifying a concentrated aqueous Orange II solution (p-(2-hydroxy-1-naphthylazo) benzene sulfonic acid/Pylam Products Inc.) with hydrochloric acid. The dye was then isolated from an aqueous-alcoholic solution by filtration, then dried. A stock solution of the acid Orange II was prepared in formic acid at a concentration of 2 mg acid Orange II per gram of reagent formic acid.

Standard Curve Preparation: A standard curve of optical density vs. dye concentration was prepared by first weighing aliquots of 0.10 g, 0.20 g, 0.30 g. 0.40 g, and 0.50 g. of stock solution into pretared 50 ml. volumetric flasks. Two milliliters of 0.20 M sodium acetate buffer (adjusted to pH 5.6 with acetic acid) were added and finally diluted to 50.00 ml with distilled water. Optical density of each was determined at 485 m$\mu$ with a Beckman DB spectrophotometer.

The standard curve was a straight line eminating from the origin, following the equation.

C=0.0024D

Where
C=mmol of H+ Orange II in test solution
D=Optical density of test solution The results obtained for each of the shampoo compositions are shown below and are compared with a commercially available conditioning shampoo.

| Sample | Mean Dye Pickup (mmol/g hair) |
|---|---|
| Test shampoo with 0% Catrex | 0.112 |
| Test shampoo with 3% Catrex | 0.125 |
| Test shampoo with 5.7% Catrex | 0.129 |
| Test shampoo with 7% Catrex | 0.138 |
| Commercial Conditioning Shampoo (containing a cationic quaternized cellulosic polymer, an anionic and an amphoteric surfactant) | 0.126 |

Hair Preparation and Exposure to Test Shampoo: Ten inch bleached blonde hair was separated into swatches of approximately 2 grams in weight. These were secured and bound at the root end with cotton thread and epoxy cement.

A swatch under test (8 per test sample) was wetted with distilled water and shampooed with approximately 0.05 g. of the test shampoo. Lather was formed and evenly distributed throughout the swatch. After a ten minute contact time, the swatch was rinsed thoroughly for one minute under 100° F. tap water. Excess water was squeezed out. Swatches were dried at 120° F. for 1 hour then equilibrated at 70° F./50% RH for 24 hours.

Dye Pickup and Measurement: Approximately one-half inch of each of the test swatches (0.10–0.15 g. hair) were cut off the unbound end and weighed onto pretared 50 ml. Erlenmeyer flasks. Twenty-five milliliters of stock dye solution were pipetted into each flask. Flasks were then stoppered and the hair was allowed to remain in contact with the dye solution for 16 hours. Robbins et al. (Textile Research Journal, 38 (11) 1968) reported that maximum pick-up is achieved under these conditions in less than 2 hours.

A 0.2 g.–0.4 g. aliquot of each sample of "exhausted dye solution" was weighed into a pretared 50 ml. volumetric flask. Two milliliters of the sodium acetate buffer solution were added and the samples were diluted with distilled water. Samples were mixed thoroughly and optical density was determined at 485 m$\mu$ with a Beckman DB spectrophotometer. The amount (mmol.) of dye adsorbed by the hair sample can be determined by the equations.

$$DP = \frac{C_I - C_F}{Wh}$$

$$C_F = .0024D \times \frac{30.5}{WA}$$

DP = dye bound by one gram hair
$C_I$ = mmol. dye in 25 ml. stock solution
$C_F$ = mmol. dye in 25 ml. "exhausted dye solution"
Wh = Weight hair sample (grams)
D = Optical density test solution
WA = Weight (grams) aliquot "exhausted dye solution"
30.5 = Weight (grams) of 25 ml. stock solution.

EXAMPLE IX

In accordance with the procedure described in Example I, shampoo compositions can be prepared using any of a variety of cationic polymers. Thus, shampoos which lather and rinse well and leave the hair manageable and full bodied may be prepared within the scope of the present invention using any of the representative polymers shown in Table IV.

TABLE IV

| Polymers | Monomer proportions mole percent |
|---|---|
| Phosphate salt of poly(aminoethyl)acrylate | — |
| Hydrochloride salt of poly(aminoethyl acrylate/acrylamide) | 50/50 |
| Phosphate salt of poly(aminoethyl acrylate/aminoethyl crotonate) | 95/5 |
| Hydrochloride salt of poly(aminoethyl methacrylate) | 100 |
| Phosphate salt of poly(2-aminopropyl acrylate/diethyl fumarate) | 75/25 |
| Phosphate salt of poly(aminoethyl acrylate/acrylamide/hydroxypropyl acrylate) | 80/4/16 |
| Phosphate salt of poly(aminoethyl acrylate/acrylamide/hydroxypropyl acrylate) | 75/15/10 |
| Phosphate salt of poly(aminoethyl acrylate/diethyl fumarate) | 85/15 |
| Phosphate salt of poly(aminoethyl maleate/vinyl methyl ether) | 50/50 |
| Phosphate salt of poly(N-ethyl aminoethyl methacrylate/dioctyl fumarate) | 80/20 |
| Sulfuric acid salt of poly(aminoethyl acrylate/monomethyl maleate) | 80/20 |
| Sulfuric acid salt of poly(N-methyl aminoethyl acrylate/ethyl acrylate) | 70/30 |
| Phosphate salt of poly(aminoethyl methacrylate/dodecyl methacrylate) | 80/20 |
| Hydrochloride salt of poly(aminoethyl acrylate/vinyl acetate) | 80/20 |

Variations may be made in the proportions, procedures, and materials without departing from the scope of this invention which is defined by the following claims.

We claim:
1. A conditioning shampoo composition consisting essentially of an aqueous solution of:
(1) from 0.1 to 10.0%, by weight of the total solution, of a water-soluble acid salt of an aminoalkyl ester of a cationic polymer having a molecular weight of 5,000 to 250,000 and selected from the group consisting of the water-soluble acid salts of aminoalkyl esters of (a) a homopolymer of a homopolymerizable unsaturated carboxylic acid having 3 to 5 carbon atoms; (b) a copolymer of a copolymerizable mixture of unsaturated carboxylic acid having 3 to 5 carbon atoms, and (c) a copolymer formed of (i) an unsaturated carboxylic acid having 3 to 5 carbon atoms and (ii) at least one copolymerizable ethylenically unsaturated comonomer selected from the group consisting of vinyl acetate, vinyl propionate, vinyl methyl ether, vinyl ethyl ether, the $C_1$-$C_8$ alkyl esters of maleic and the $C_1$-$C_8$ alkyl esters of fumaric acids, an amide of acrylic acid and an amide of methacrylic acid, $C_1$-$C_{18}$ alkyl ester of acrylic acid, a $C_1$-$C_{18}$ alkyl ester of methacrylc acid, a $C_2$-$C_4$ hydroxyl-alkyl ester of acrylic acid and a $C_2$-$C_4$ hydroxyalkylester of methacrylic acid, wherein the copolymers of group (c) are prepared with at least 50 mole percent of the unsaturated carboxylic acid component (i); and

(2) from 5.0 to 30.0%, by weight active solids, based on the weight of the total solution, of at least one anionic surfactant selected from the group consisting of a higher fatty alcohol sulfate, an alkylaryl sulfonate, an alkali metal higher alkyl sulfosuccinate, and an alkali metal salt of an alkylarylpolyethoxyethanol sulfate or an alkali metal salt of an alkylarylpoly-ethoxyethanol sulfonate, said shampoo composition being prepared in the absence of an amphoteric surfactant and characterized by depositing the cationic polymer on the hair during use, rendering the hair to be more manageable.

2. The shampoo composition of claim 1 wherein the cationic polymer is a phosphate salt of a poly(aminoethyl acrylate), or of poly(aminoethyl acrylate hydroxypropyl acrylate) or of a terpolymer of an aminoalkyl ester of an ethylenically unsaturated carboxylic acid, an amide of an ethylenically unsaturated carboxylic acid, and a hydroxyalkyl ester of an ethylenically unsaturated carboxylic acid, and wherein said cationic polymer has a molecular weight between about 25,000 and 100,000.

3. The shampoo composition of claim 1 wherein the anionic surfactant component comprises at least one member selected from the group consisting of sodium lauryl sulfate, sodium lauryl ether sulfate, triethanolamine lauryl sulfate, sodium isopropylbenzene sulfonate, potassium isopropylbenzene sulfonate, isopropyl naphthalene sulfonate, sodium octenyl sulfosuccinate, disodium salt of a sulfosuccinate half ester of an alkanolamide, fatty alcohol ether sulfosuccinate, sodium N-methyl-N-palmitoyl taurate, sodium oleyl isethionate, and the sodium t-octyl phenoxypolyethoxyethyl sulfates and sulfonates containing 1 to 5 oxyethylene units.

4. The shampoo composition of claim 1 comprising 0.5 to 2.0% by weight of the total solution of the cationic polymer, 10.0–20.0% by weight active solids based on the weight of the total solution of at least one anionic surfactant, and 2.0 to 8.0% by weight active solids based on the weight of the total solution of at least one nonionic surfactant.

5. The shampoo composition of claim 1 wherein the copolymer of group (c) is prepared with at least 75 mole percent of the unsaturated carboxylic acid component.

6. The shampoo composition of claim 1 further comprising 0 to 10.0%, by weight active solids, based on the weight of the total solution, of at least one nonionic surfactant.

7. The shampoo composition of claim 1 wherein said water-soluble acid salt is an inorganic acid salt.

* * * * *